United States Patent
Sato et al.

(10) Patent No.: US 12,240,796 B2
(45) Date of Patent: Mar. 4, 2025

(54) CRYSTALS AND PRODUCTION METHOD FOR THE SAME

(71) Applicant: OTSUKA CHEMICAL CO., LTD., Osaka (JP)

(72) Inventors: Eriko Sato, Tokushima (JP); Noriaki Shiina, Tokushima (JP); Mifuyu Ueno, Tokushima (JP)

(73) Assignee: OTSUKA CHEMICAL CO., LTD., Osaka (JP)

(*) Notice: Subject to any disclaimer, the term of this patent is extended or adjusted under 35 U.S.C. 154(b) by 0 days.

(21) Appl. No.: 17/786,731

(22) PCT Filed: Dec. 18, 2020

(86) PCT No.: PCT/JP2020/047326
§ 371 (c)(1),
(2) Date: Jun. 17, 2022

(87) PCT Pub. No.: WO2021/125306
PCT Pub. Date: Jun. 24, 2021

(65) Prior Publication Data
US 2023/0022116 A1  Jan. 26, 2023

(30) Foreign Application Priority Data
Dec. 20, 2019 (JP) .................. 2019-230664

(51) Int. Cl.
*C07C 243/38* (2006.01)
*B60C 1/00* (2006.01)
*C08K 5/25* (2006.01)

(52) U.S. Cl.
CPC .............. *C07C 243/38* (2013.01); *B60C 1/00* (2013.01); *C08K 5/25* (2013.01); *C07B 2200/13* (2013.01)

(58) Field of Classification Search
CPC ............................ C07C 251/76; C07C 243/38
See application file for complete search history.

(56) References Cited

U.S. PATENT DOCUMENTS

| | | |
|---|---|---|
| 6,380,288 B1 | 4/2002 | Hojo et al. |
| 2003/0175607 A1 | 9/2003 | Isoda et al. |
| 2020/0263001 A1 | 8/2020 | Yoshizawa et al. |

FOREIGN PATENT DOCUMENTS

| | | | |
|---|---|---|---|
| EP | 3 805 306 | | 4/2021 |
| JP | 9-124840 | | 5/1997 |
| JP | 10-330549 | | 12/1998 |
| JP | 11-292834 | | 10/1999 |
| JP | 2000-190704 | | 7/2000 |
| JP | 2003-183510 | | 7/2003 |
| JP | 2009131737 A | * | 6/2009 |
| JP | 2019-6845 | | 1/2019 |
| WO | 2017/104467 | | 6/2017 |
| WO | 2019/235526 | | 12/2019 |

OTHER PUBLICATIONS

Machine translation of JP 2009-131737 (2009, 9 pages).*
International Preliminary Report on Patentability and Written Opinion of the International Searching Authority issued May 17, 2022 in International (PCT) Application No. PCT/JP2020/047326.
International Search Report (ISR) issued Feb. 9, 2021 in International (PCT) Application No. PCT/JP2020/047326.
Office Action issued Sep. 24, 2024 in Japanese Patent Application No. 2021-565667, with English-language translation.
Maeda, Morikazu, "Designing Formulation (2), Types and properties of compounding agents", The Society of Rubber Industry, Japan, 1978, vol. 51, No. 10, pp. 808-812, with partial English-language translation.

* cited by examiner

*Primary Examiner* — Brieann R Johnston
(74) *Attorney, Agent, or Firm* — Wenderoth, Lind & Ponack, L.L.P.

(57) ABSTRACT

An object of the present invention is to provide novel crystals. Provided are crystals of 3-hydroxy-N'-(1,3-dimethylbutylidene)-2-naphthoic acid hydrazide having an X-ray powder diffraction pattern comprising a peak of maximum intensity at an angle of diffraction (2θ) of 6.1±0.2°.

13 Claims, 2 Drawing Sheets

CRYSTALS AND PRODUCTION METHOD FOR THE SAME

TECHNICAL FIELD

The present invention relates to novel crystals etc.

BACKGROUND ART

Rubber products, such as tires, contain various additives. For example, a hydrazide compound is used as a rubber additive (for example, see patent literature 1).

CITATION LIST

Patent Literature

Patent literature 1: JP 2019-6845 A

SUMMARY OF INVENTION

Technical Problem

An object of the present invention is to provide novel crystals.

Another object of the present invention is to provide a novel method for producing the crystals.

Another object of the present invention is to provide a novel rubber additive.

Solution to Problem

The inventors conducted extensive studies to solve the above problems focusing on 3-hydroxy-N'-(1,3-dimethylbutylidene)-2-naphthoic acid hydrazide, and found that novel crystals of the compound can be obtained by appropriately selecting the conditions for precipitation of the crystals (i.e., crystallization).

The inventors also found that the novel crystals include various types of crystals that impart different properties to a rubber component when used as rubber additives.

The inventors further found that, among the novel crystals, the crystals according to the present invention have lower heat build-up and better processability as compared with other crystals. The inventors made further studies and completed the present invention.

That is, the present invention relates to the following.
(1) Crystals of 3-hydroxy-N'-(1,3-dimethylbutylidene)-2-naphthoic acid hydrazide having an X-ray powder diffraction pattern comprising a peak of maximum intensity at an angle of diffraction (2θ) of 6.1±0.2°.
(2) Crystals of 3-hydroxy-N'-(1,3-dimethylbutylidene)-2-naphthoic acid hydrazide having an X-ray powder diffraction pattern comprising characteristic peaks at least at angles of diffraction (2θ) of 6.1±0.2°, 17.7±0.2°, 17.9±0.2° and 19.1±0.2°.
(3) The crystals according to the above (2), wherein the crystals have an X-ray powder diffraction pattern comprising characteristic peaks at least at angles of diffraction (2θ) of 6.1±0.2°, 17.7±0.2°, 17.9±0.2°, 18.2±0.2°, 19.1±0.2° and 23.8±0.2°.
(4) The crystals according to any one of the above (1) to (3), wherein the crystals have a melting point of 148° C. or more.
(5) A rubber additive comprising the crystals according to any one of the above (1) to (4).
(6) A rubber composition comprising the rubber additive according to the above (5).
(7) A tire comprising the rubber composition according to the above (6).
(8) A method for producing the crystals according to any one of the above (1) to (4), the method comprising bubbling oxygen gas or an oxygen-containing gas into a solution containing 3-hydroxy-N'-(1,3-dimethylbutylidene)-2-naphthoic acid hydrazide.
(9) A method for improving low heat build-up and/or processability of a rubber, the method comprising using the crystals according to any one of the above (1) to (4) to improve low heat build-up and/or processability of a rubber.
(10) Use of the crystals according to any one of the above (1) to (4) for improvement of low heat build-up and/or processability of a rubber.

Advantageous Effects of Invention

The present invention provides novel crystals, in particular, novel crystals of 3-hydroxy-N'-(1,3-dimethylbutylidene)-2-naphthoic acid hydrazide.

The present invention also provides a novel rubber additive comprising the crystals.

The rubber additive is capable of imparting low heat build-up properties to a rubber component. Thus, a rubber composition comprising the rubber additive can be used to produce a rubber product (such as a tire) with low heat build-up.

In general, a rubber component with low heat build-up tends to have poor processability. However, the rubber additive according to the invention achieves both low heat build-up and good processability.

The present invention also provides a novel method for producing the crystals.

DESCRIPTION OF EMBODIMENTS

Crystals

Figure 1:
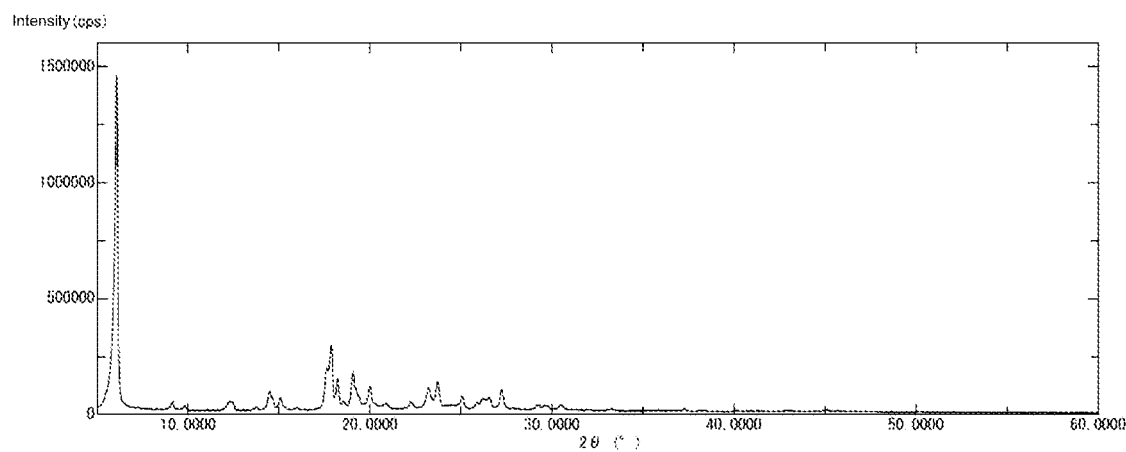
FIG. 1 shows the results of X-ray powder diffraction analysis in Example 1.

The crystals of 3-hydroxy-N'-(1,3-dimethylbutylidene)-2-naphthoic acid hydrazide of the present invention (also simply called the crystals of the present invention) may have an X-ray powder diffraction pattern comprising a peak of maximum intensity at an angle of diffraction (2θ) of, for example, 6.1° as analyzed with a powder X-ray diffractometer using Cu-Kα rays (wavelength λ=1.54 angstroms) as described in Examples below.

The crystals of the present invention may also have an X-ray powder diffraction pattern comprising characteristic peaks at angles of diffraction (2θ) of, for example, 6.1°, 17.7°, 17.9°, 18.2°, 19.1° and 23.8° as analyzed with a powder X-ray diffractometer using Cu-Kα rays (wavelength λ=1.54 angstroms).

The crystals of the present invention may also have an X-ray powder diffraction pattern comprising characteristic peaks at least at angles of diffraction (2θ) of 6.1°, 17.7°, 17.9° and 19.1°, or may have an X-ray powder diffraction pattern comprising characteristic peaks at least at angles of diffraction (2θ) of 6.1°, 17.7°, 17.9°, 18.2°, 19.1° and 23.8°, as analyzed with a powder X-ray diffractometer using Cu-Kα rays (wavelength λ=1.54 angstroms).

In general, an angle of diffraction (2θ) measured by X-ray powder diffractometry may vary to some extent depending on the measurement conditions. Thus the crystals of 3-hydroxy-N'-(1,3-dimethylbutylidene)-2-naphthoic acid hydrazide according to the invention include crystals having peaks at angles of diffraction corresponding to the angles of diffraction described above within the margin of error as measured by X-ray powder diffractometry. This error in the measurement of angles of diffraction may be, for example, ±0.2°. That is, the crystals of the present invention include crystals having peaks at angles of diffraction corresponding to the angles of diffraction described above with an error of ±0.2°. Unless otherwise specified herein, the angles of diffraction described herein are construed as angles of diffraction measured with an error of ±0.2°.

The "angle of diffraction (2θ)±0.2°" herein indicates (2θ−0.2°)≤2θ≤(2θ+0.2°). That is, it means that the angle of diffraction ranges from (2θ−0.2°) to (2θ+0.2°).

When the region of the diffraction angle of a peak overlaps with the region of the diffraction angle of another peak, these peaks may overlap with each other. For example, a peak at 2θ of 17.7°±0.2° overlaps with a peak at 2θ of 17.9°±0.2° in the angle region from 17.7° to 17.9°, and two distinct peaks may be present in the angle region from 17.7° to 17.9°, or two peaks may overlap with each other in the region from 17.7° to 17.9°.

The crystals of the present invention may have peaks with an intensity of 5% or more at least at angles of diffraction (2θ) of 17.7°, 17.9°, 18.2°, 19.1° and 23.8° relative to the intensity of the peak at an angle of diffraction (2θ) of 6.1° taken as 100%.

The crystals of the present invention may have peaks with an intensity of 8% or more at least at angles of diffraction (2θ) of 17.7°, 17.9° and 23.8° relative to the intensity of the peak at an angle of diffraction (2θ) of 6.1° taken as 100%.

The crystals of the present invention may have a peak with an intensity of 10% or more (for example, 11 to 24%) at least at an angle of diffraction (2θ) of 17.9° relative to the intensity of the peak at an angle of diffraction (2θ) of 6.1° taken as 100%.

The crystals of the present invention may have a peak with an intensity of 8 to 15% at an angle of diffraction (2θ) of 17.7° relative to the intensity of the peak at an angle of diffraction (2θ) of 6.1° taken as 100%.

The peaks may have a different intensity from those described above.

The melting point or endothermic peak of the crystals of the present invention is, for example, 147° C. or more, preferably 148° C. or more, more preferably 148 to 151° C., and further preferably 148.5 to 150.5° C., as determined by differential scanning calorimetry (DSC).

The crystals of the present invention may be in any form, and may be in the form of aggregates or a pulverized powder obtained by appropriate means.

The mean particle size of the crystals of the present invention determined as a particle size at 50% ($D_{50}$) in the cumulative distribution of the number of particles may be, for example, 0.5 μm or more, and is preferably 5 to 50 μm, and more preferably 10 to 30 μm, but not limited thereto.

When the crystals are in the form of aggregates, the mean particle size of the crystals may be appropriately adjusted to the above range by means of, for example, pulverization.

When the crystals of the present invention are in the form of a pulverized powder, the mean particle size ($D_{50}$) may be, for example, 0.5 μm or more, and is preferably 5 to 50 μm, and more preferably 10 to 30 μm.

The mean particle size ($D_{50}$) may be determined by any method, including the method described in Examples below.

The specific surface area of the crystals of the present invention may be, for example, 0.4 to 3.0 m²/g, and is preferably 0.5 to 2.5 m²/g, and more preferably 0.8 to 1.4 m²/g, but not limited thereto.

The specific surface area may be determined by any method, including the method described in Examples below.

The crystals of the present invention may have any shape, including a plate shape, a pillar shape and an acicular shape, and may preferably have a plate shape.

The crystals of the present invention may contain different crystalline forms (polymorphs) of 3-hydroxy-N'-(1,3-dimethylbutylidene)-2-naphthoic acid hydrazide without departing from the scope of the invention.

The crystals of the present invention can be produced by, for example, the production method described below.

Production Method

The crystals of the present invention can be produced by contacting a solution containing 3-hydroxy-N'-(1,3-dimethylbutylidene)-2-naphthoic acid hydrazide (also simply called "compound A") (this solution may also be simply called the "solution of compound A") with oxygen (this step may also be called the "contacting step").

The solution of compound A may be any solution that contains compound A dissolved in a solvent, and may be a reaction mixture containing the produced compound A.

Examples of the solvent for dissolution of compound A include alcohols, such as isopropyl alcohol and butanol; hydrocarbons, such as heptane and toluene; esters, such as butyl acetate; and methyl isobutyl ketone. These solvents may be used alone or in combination of two or more of them.

The reaction mixture containing the produced compound A may be, for example, a reaction mixture containing compound A produced from 3-hydroxy-2-naphthoic acid hydrazide and methyl isobutyl ketone as precursors of compound A.

Examples of the solvent used in the reaction include alcohols, such as isopropyl alcohol and butanol; hydrocarbons, such as heptane and toluene; esters, such as butyl acetate; and methyl isobutyl ketone. These solvents may be used alone or in combination of two or more of them. Methyl isobutyl ketone, which serves as a reaction precursor, is preferred as the solvent.

The amount (concentration) of compound A in the solution of compound A may be, for example, 20% by mass or more, and is preferably 25% by mass or more, and further preferably 30% by mass or more. For efficient production of the crystals of the present invention, the concentration of compound A in the solution may be, for example, 50% by mass or less, and is preferably 35% by mass or less.

Preferably, the solution of compound A is typically heated to 70° C. or more, preferably 75° C. or more, further preferably 80° C. or more, to facilitate complete dissolution of compound A.

The reaction for producing compound A from 3-hydroxy-2-naphthoic acid hydrazide and methyl isobutyl ketone is performed under heating, and thus the heated reaction mixture can be directly used as the solution of compound A. When methyl isobutyl ketone is used as the solvent for the reaction, the reaction mixture can be heated to 110° C. or more and thus is suitable as the solution of compound A.

The oxygen contacted with the solution of compound A may be in any form, and may be in a gaseous form or in a liquid form. Gaseous oxygen is preferred. Examples of the gaseous oxygen include oxygen gas and an oxygen-containing gas (for example, air or a mixed gas with an inert gas, such as a mixed gas of argon and oxygen). Air is preferred due to easy handling and economic efficiency.

The contact of the solution of compound A with oxygen can be achieved by any suitable procedure that allows the solution of compound A to make contact with oxygen at the interface therebetween. For example, the contact can be achieved by allowing the solution of compound A to stand in the presence of oxygen gas or an oxygen-containing gas; or by stirring the solution of compound A in the presence of oxygen gas or an oxygen-containing gas; or by introducing oxygen gas or an oxygen-containing gas into the solution of compound A by bubbling the gas into the solution. A preferred procedure is the introduction of oxygen gas or an oxygen-containing gas into the solution of compound A by bubbling the gas into the solution because this procedure is advantageous in that, for example, the solution of compound A is efficiently in contact with oxygen.

That is, the present invention includes a method for producing the crystals of compound A, the method comprising bubbling oxygen gas or an oxygen-containing gas into a solution of compound A. In particular, the present invention includes a method for producing the crystals of compound A, the method comprising bubbling oxygen gas or an oxygen-containing gas into a solution of compound A, and crystallizing the compound A.

The amount of oxygen used in the contacting step may be, for example, 0.001 mol or more, and is preferably 0.01 mol or more, relative to 1 mol of compound A, but not limited thereto. The maximum amount of oxygen is not specifically defined.

The duration of the contact of the solution of compound A with oxygen is typically 0.1 hours or more, preferably 0.5 hours or more, and further preferably 1 hour or more, and may be, for example, 72 hours or less, and is preferably 48 hours or less, and further preferably 24 hours or less. When the solution of compound A is made in contact with oxygen by bubbling, the solvent in the solution may be evaporated during the bubbling. To address this problem, the bubbling procedure is preferably followed by stopping the bubbling and allowing the solution to stand or stirring the solution.

When the contacting step is performed at a temperature near the boiling point of the solvent in the solution of compound A, the evaporation of the solvent may prevent the contact of compound A with oxygen. Thus, the contacting step is preferably performed at a temperature lower than the boiling point of the solvent in the solution of compound A. Compound A is also preferably maintained in a completely dissolved state during the contacting step, and thus the temperature during the contacting step is appropriately set at typically 70° C. or more, preferably 75° C. or more, further preferably 80° C. or more.

Preferably, the precipitation of crystals or crystallization is initiated immediately after the completion of the contacting step.

In cases where crystallization is observed during the contacting step, the precipitated crystals are preferably dissolved again by heating after the completion of the contacting step, and then recrystallized to produce the crystals of the present invention at high purity.

The crystallization may be performed by adding a poor solvent to the solution of compound A to precipitate the crystals, or by cooling the solution of compound A to precipitate the crystals.

The poor solvent used in the crystallization by adding a poor solvent to the solution of compound A may be any solvent that facilitates the crystallization from the solution of compound A, including, for example, ether solvents, such as diethyl ether, diisopropyl ether, tetrahydrofuran (THF), and 1,4-dioxane; and aliphatic or alicyclic hydrocarbon solvents, such as pentane, hexane, cyclohexane, and petroleum ether. These solvents may be used alone or in combination of two or more of them.

The amount of the poor solvent used in the crystallization varies depending on the conditions such as the type of solvent in the solution of compound A, the amount of the solvent and the crystallization temperature, and can be appropriately adjusted while observing the progress of crystallization.

In the crystallization by cooling the solution of compound A, the cooling rate is adjusted so that the crystals are efficiently precipitated and other advantages are obtained, and may be, for example, 0.5 to 30° C./min, and is preferably 0.5 to 20° C./min, and more preferably 0.5 to 10° C./min, but not limited thereto.

The cooling temperature may be, for example, 40° C. or less, or 30° C. or less, and is preferably 15° C. or less, and further preferably 10° C. or less, but not limited thereto. Aging of the crystals may also be performed at these temperatures.

Aging of the crystals may be performed by, for example, stirring the solution of compound A or allowing the solution of compound A to stand without addition of any other components. The aging time may be, for example, 0.1 minutes to 3 hours, and is preferably 1 minute to 1 hour, and further preferably 5 to 30 minutes, but not limited thereto.

The crystallization procedure by cooling the solution of compound A to precipitate the crystals is preferred due to operating efficiency, cost efficiency, the purity of the resulting crystals, and other advantages.

The crystallization may be performed by adding seed crystals of compound A.

The seed crystals may separately be prepared in advance in accordance with the production method of the present invention.

The amount of the seed crystals may be 10% by mass or less (for example, 0.05 to 10% by mass, 0.1 to 8% by mass, or 0.1 to 5% by mass) relative to the mass of the substrate (compound A), but is not limited thereto.

The crystals prepared by the production method as described above may be isolated by conventional solid-liquid separation (for example, filtration or centrifugation).

The crystals of the present invention produced as above may be appropriately used as a rubber additive, but the application of the crystals is not limited thereto.

Accordingly, the present invention includes a rubber additive comprising the crystals of the present invention.

The rubber additive of the present invention may be appropriately used in a rubber composition, but the application of the rubber additive is not limited thereto.

Accordingly, the present invention includes a rubber composition comprising the rubber additive of the present invention.

Such a rubber composition is also defined as a composition comprising the crystals of the present invention (or a composition comprising compound A comprising the crystals of the present invention).

The rubber composition of the present invention comprises at least the crystals of the present invention and may further comprise crystals other than the crystals of the present invention without departing from the scope of the invention.

The amount of the crystals of the present invention contained in compound A may be, for example, 30% by mass or more, 40% by mass or more, 50% by mass or more, 60% by mass or more, 70% by mass or more, 80% by mass or more, or 90% by mass or more, but is not limited thereto.

Rubber Composition

The rubber composition may comprise a rubber component.

Examples of the rubber component include, but are not limited to, diene rubbers, such as polybutadiene rubber, isoprene rubber, styrene-butadiene rubber, styrene-isoprene-butadiene rubber, chloroprene rubber, and acrylonitrile-butadiene rubber; and non-diene rubbers, such as ethylene-propylene rubber and butyl rubber. These rubber components may be a natural or synthetic rubber.

These rubber components may be used alone or in combination of two or more of them.

The rubber component contained in the rubber composition of the invention is preferably a diene rubber, in particular, preferably a natural diene rubber.

The amount of the diene rubber contained as the rubber component is selected so that improved low heat build-up properties are maintained and other advantages are obtained, and is preferably 80% by mass or more and more preferably 90% by mass or more, but not limited thereto.

The rubber composition in the invention may further contain an additive other than the rubber additive of the invention.

The additional additive may be any additive commonly used in the rubber industry.

Examples of the additional additive include an antioxidant, such as a hydrazide compound other than compound A, a phenolic antioxidant, an imidazole antioxidant, and an amine antioxidant; a filler, including inorganic fillers, such as a white filler (for example, silica, a silicate, a carbonate or a metal oxide), and organic fillers, such as carbon black; a vulcanizing agent, such as sulfur; a process oil, such as a paraffinic process oil, a naphthene process oil, and an aromatic process oil; a vulcanization accelerator, such as a thiazole vulcanization accelerator and a sulfenamide vulcanization accelerator; a vulcanization acceleration aid, such as zinc oxide and a fatty acid (for example, stearic acid); an oxidation inhibitor; an antiozonant; and a silane coupling agent.

These additional additives may be used alone or in combination of two or more of them.

The amount of the rubber additive of the invention (or the crystals of the present invention, or compound A comprising the crystals of the present invention) contained in the rubber composition is selected so that low heat build-up properties, good processability and other properties are obtained, and may be, for example, 0.05 to 30 parts by mass, and is preferably 0.05 to 10 parts by mass, and more preferably 0.05 to 5 parts by mass, relative to 100 parts by mass of the rubber component, but not limited thereto.

The amount of the rubber additive of the invention (or the crystals of the present invention, or compound A comprising the crystals of the present invention) contained in the rubber composition is selected so that low heat build-up properties, good processability and other properties are obtained, and may be, for example, 0.02 to 18% by mass, and is preferably 0.02 to 6% by mass, and more preferably 0.02 to 3% by mass, relative to the total mass of the rubber composition, but not limited thereto.

The amount of the rubber component contained in the rubber composition of the invention is appropriately selected depending on the intended use of the rubber composition. For example, when the rubber composition is used to prevent the reduction of the elasticity of a rubber and maintain the elasticity, the amount of the rubber component is preferably 30 to 99% by mass, more preferably 40 to 80% by mass, relative to 100% by mass of the rubber composition.

Filler

The rubber composition of the present invention typically further contains a filler as an additive in addition to the rubber component as described above.

When the rubber composition contains a filler together with the rubber component and the crystals of the present invention, the dispersibility of the filler is improved, and the rubber composition maintains high strength, high abrasion resistance and other properties and achieves improved low heat build-up properties even in the presence of the filler.

The amount of the filler is preferably 10 to 160 parts by mass, more preferably 30 to 100 parts by mass, relative to 100 parts by mass of the rubber component, but not limited thereto. The rubber composition containing the optimized amount of the filler has further improved low heat build-up and further improved abrasion resistance. When the amount of the filler is 10 parts by mass or more, sufficient abrasion resistance is achieved. When the amount of the filler is 160 parts by mass or less, deterioration of low heat build-up properties is prevented.

The amount of the filler contained in the rubber composition is selected so that low heat build-up properties, abrasion resistance and other properties are obtained, and may be, for example, 1,000 to 16,000 parts by mass, and is preferably 2,000 to 10,000 parts by mass, and more preferably 3,000 to 7,000 parts by mass (for example, 4,000 to 6,000 parts by mass), relative to 100 parts by mass of the rubber additive of the invention (or the crystals of the present invention, or compound A comprising the crystals of the present invention), but not limited thereto.

The filler may be any type, and examples thereof include those exemplified above (including carbon black and silica). Carbon black is particularly preferred, which contributes to further improved low heat build-up properties, abrasion resistance and other properties.

The carbon black includes GPF, FEF, SRF, HAF, ISAF, IISAF, or SAF class carbon blacks.

The amount of the carbon black contained in the rubber composition is selected so that further improved abrasion resistance and other properties are obtained, and is preferably 10 parts by mass or more, more preferably 30 parts by mass or more, and further preferably 50 parts by mass or more, relative to 100 parts by mass of the rubber component.

The amount of the carbon black contained in the rubber composition is selected so that further improved low heat build-up properties and processability are obtained while maintaining high abrasion resistance, and is preferably 160 parts by mass or less, more preferably 90 parts by mass or less, and further preferably 70 parts by mass or less, relative to 100 parts by mass of the rubber component.

Carbon black tends to deteriorate low heat build-up properties and processability. However, the crystals of the present invention achieve both low heat build-up and processability, and thus a relatively large amount of carbon black can be added to the rubber composition to enhance the fracture resistance of the rubber.

The silica serving as a filler may be, for example, wet silica, dry silica, or colloidal silica, but is not limited thereto.

The inorganic filler may be, for example, an inorganic compound represented by formula (I):

$$nM \cdot xSiO_y \cdot zH_2O \qquad (I).$$

wherein M is at least one selected from the group consisting of metals selected from the group consisting of Al, Mg, Ti, Ca, and Zr, oxides or hydroxides of the metals, hydrates thereof, and carbonates of the metals; n is an integer of 1 to 5; x is an integer of 0 to 10; y is an integer of 2 to 5; and z is an integer of 0 to 10.

Examples of the inorganic compound of formula (I) include aluminas ($Al_2O_3$), such as γ-alumina and α-alumina; alumina monohydrates ($Al_2O_3 \cdot H_2O$), such as boehmite and diaspore; aluminum hydroxides [$Al(OH)_3$], such as gibbsite and bayerite; aluminum carbonate [$Al_2(CO_3)_3$]; magnesium hydroxide [$Mg(OH)_2$]; magnesium oxide (MgO); magnesium carbonate ($MgCO_3$); talc ($3MgO \cdot 4SiO_2 \cdot H_2O$); attapulgite ($5MgO \cdot 8SiO_2 \cdot 9H_2O$); titanium white ($TiO_2$); titanium black ($TiO_{2n-1}$); calcium oxide (CaO); calcium hydroxide [$Ca(OH)_2$]; aluminum magnesium oxide ($MgO \cdot Al_2O_3$); clay ($Al_2O_3 \cdot 2SiO_2$); kaolin ($Al_2O_3 \cdot 2SiO_2 \cdot 2H_2O$); pyrophyllite ($Al_2O_3 \cdot 4SiO_2 \cdot H_2O$); bentonite ($Al_2O_3 \cdot 4SiO_2 \cdot 2H_2O$); aluminum silicates, such as $Al_2SiO_5$ and $Al_4 \cdot 3SiO_4 \cdot 5H_2O$; magnesium silicates, such as $Mg_2SiO_4$ and $MgSiO_3$; calcium silicates, such as $Ca_2SiO_4$; aluminum calcium silicates, such as $Al_2O_3 \cdot CaO \cdot 2SiO_2$; magnesium calcium silicate ($CaMgSiO_4$); calcium carbonate ($CaCO_3$); zirconium oxide ($ZrO_2$); zirconium hydroxide [$ZrO(OH)_2 \cdot nH_2O$]; zirconium carbonate [$Zr(CO_3)_2$]; various zeolites; and crystalline aluminosilicates containing an alkali metal or an alkaline earth metal.

The rubber composition may be produced by any method, for example, by kneading the components of the rubber composition. Kneading may be performed by any method, for example, by a conventional method using a kneader, such as a roller, an internal mixer, or a Banbury mixer.

The components of the rubber composition may be subjected to kneading in any order. For example, all the components may be kneaded at once, or some of the components may be previously kneaded, and then the remaining components may be kneaded.

The rubber composition of the invention can be vulcanized to give a rubber. The vulcanization may be performed by any method including a conventional method.

The rubber can be used for any applications and, in particular, may be appropriately used to produce tires (for example, a tread, a shoulder, a sidewall, a bead and a carcass of tires).

Accordingly, the present invention also includes a tire (for example, a pneumatic tire) comprising the rubber composition.

The tire may be produced by any method including a conventional method.

EXAMPLES

The present invention will be specifically described below with reference to Examples, but the present invention is not limited thereto.

X-Ray Powder Diffraction Analysis

The structure of crystals was determined using an X-ray diffractometer (Rigaku Corporation, Ultima IV) with an X-ray tube with a Cu target (wavelength λ=1.54059 angstroms) under conditions of a tube voltage of 40 kV, a tube current of 40 mA, a sampling width of 0.02° and a scanning speed of 30°/min.

Melting Point

The melting point of crystals was determined from the onset temperature of the endothermic peak measured with a differential scanning calorimeter (Seiko Instruments, DSC6200) while elevating the temperature from 50° C. to 170° C. at a rate of 10° C./min under a nitrogen stream.

Mean Particle Size ($D_{50}$)

The mean particle size of crystals was determined as a particle size at 50% ($D_{50}$) in the cumulative distribution from sieve analysis with a laser diffraction particle size distribution analyzer HELOS & RODOS (Sympatec).

Specific Surface Area

The specific surface area of crystals was determined by the BET method with TriStar II (Micromeritics).

Example 1

To a reaction vessel equipped with a Dean-Stark reflux condenser and a stirrer, 200 mL of methyl isobutyl ketone and 35 g of 3-hydroxy-2-naphthoic acid hydrazide (HNH) were added so that the concentration of HNH was 17.9% by mass. The mixture was heated to about 116° C. and refluxed for 4 hours while removing the distilled water. The reaction mixture was then cooled to 100° C. and stirred at 250 rpm for 3 hours while bubbling air into the mixture with an air pump. The reaction mixture was cooled at a rate of 0.8° C./min under stirring at 250 rpm, which caused the precipitation of nuclei at 35° C. The reaction mixture was rapidly cooled to 10° C., and the precipitated crystals were filtered off and dried under reduced pressure to give light brown crystals (a-1).

Figure 3:
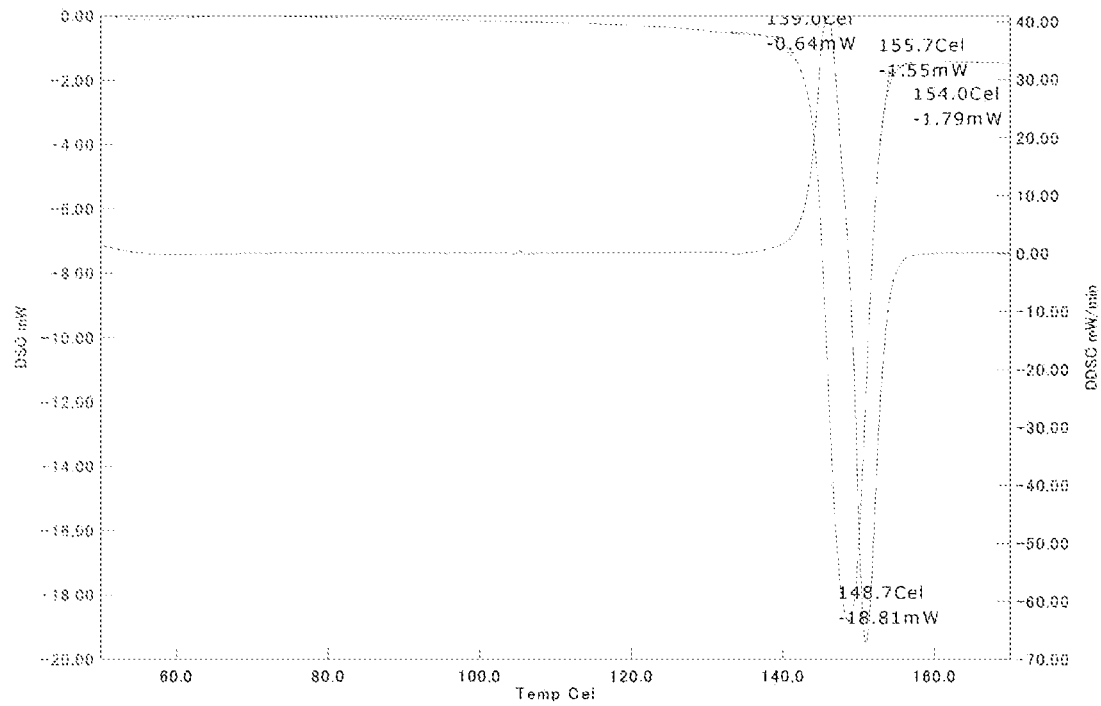
FIG. 3 shows the results of melting point analysis of crystals of Example 1.

The crystals (a-1) had a melting point of 148.7° C. as determined by DSC (FIG. 3), a specific surface area of 1.04 $m^2/g$, and a mean particle size ($D_{50}$) of 15.3 μm and had a plate shape.

The results of X-ray powder diffraction analysis of the crystals (a-1) are shown in FIG. 1 and Table 1.

TABLE 1

| 2θ (°) | Relative intensity |
|---|---|
| 6.1 | 100 |
| 17.7 | 13 |
| 17.9 | 21 |
| 18.2 | 9 |
| 19.1 | 17 |
| 23.8 | 9 |

Example 2

To a reaction vessel equipped with a Dean-Stark reflux condenser and a stirrer, 200 mL of methyl isobutyl ketone and 35 g of 3-hydroxy-2-naphthoic acid hydrazide (HNH) were added so that the concentration of HNH was 17.9% by mass. The mixture was heated to about 116° C. and refluxed for 4 hours while removing the distilled water. The reaction mixture was then cooled to 80° C. and stirred at 250 rpm for 3 hours while bubbling air into the mixture with an air pump. The reaction mixture was maintained at the same temperature in the presence of air for 21 hours. The reaction mixture was cooled at a rate of 5.5° C./min under stirring at 250 rpm, which caused the precipitation of nuclei at 35° C. The reaction mixture was rapidly cooled to 10° C., and the precipitated crystals were filtered off and dried under reduced pressure to give light brown crystals (a-2).

Figure 4:
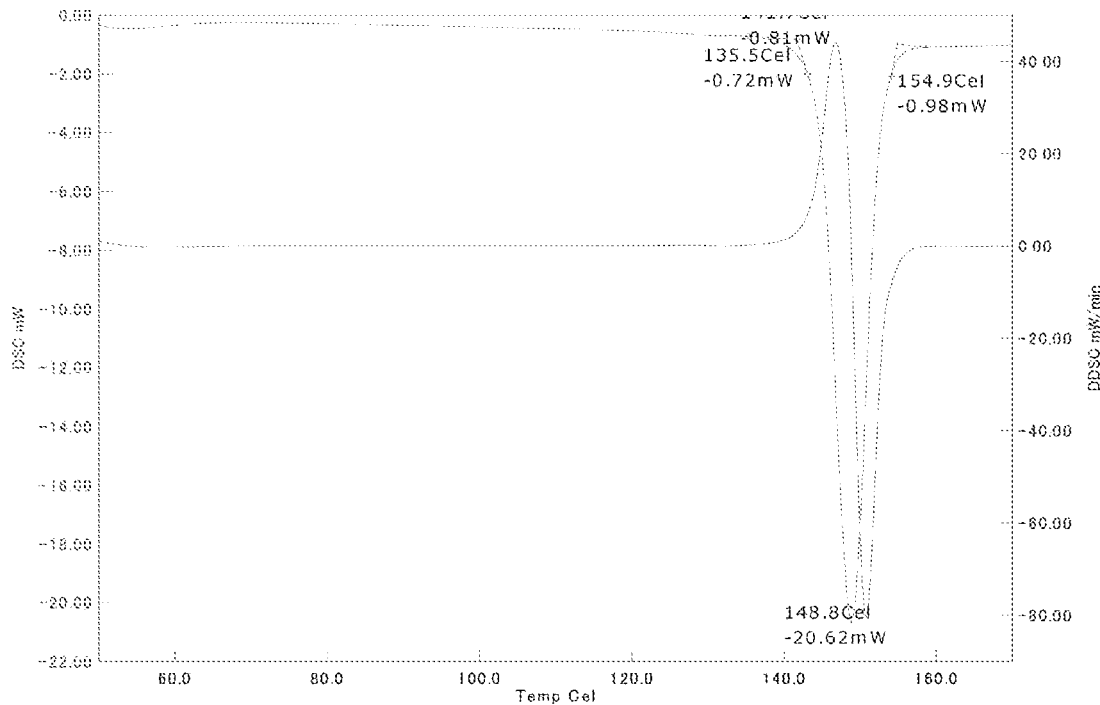
FIG. 4 shows the results of melting point analysis of crystals of Example 2.

The crystals (a-2) had a melting point of 148.8° C. as determined by DSC (FIG. 4), a specific surface area of 1.21 $m^2/g$, and a mean particle size ($D_{50}$) of 11.8 μm and had a plate shape.

Figure 2:
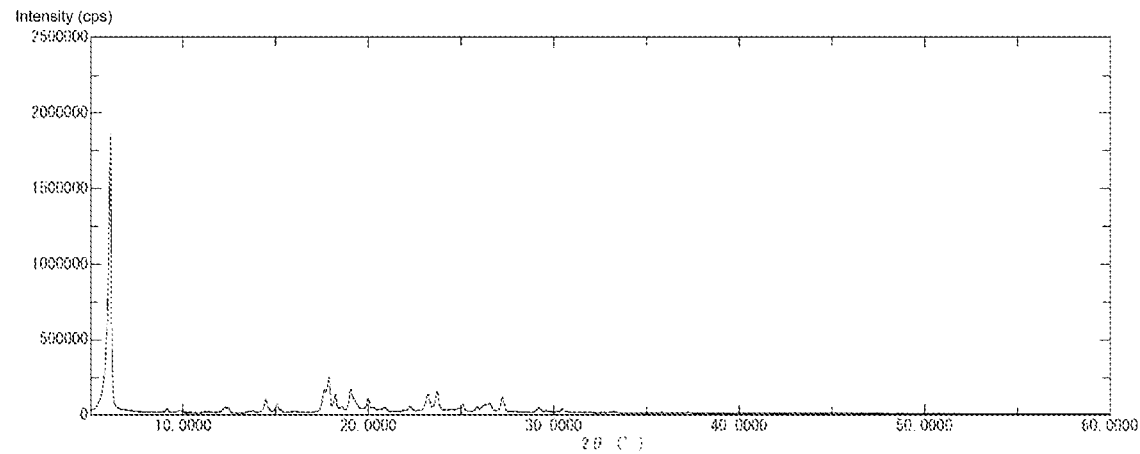
FIG. 2 shows the results of X-ray powder diffraction analysis in Example 2.

The results of X-ray powder diffraction analysis of the crystals produced in Example 2 are shown in FIG. 2 and Table 2.

TABLE 2

| 2θ (°) | Relative intensity |
|---|---|
| 6.1 | 100 |
| 17.7 | 9 |
| 17.9 | 13 |
| 18.2 | 6 |
| 19.1 | 13 |
| 23.8 | 8 |

As is clear from FIG. 1 and Table 1, the crystals (a-1) of Example 1 had a peak of maximum intensity at 6.1°.

The crystals (a-1) of Example 1 had characteristic peaks at 6.1°, 17.7°, 17.9°, 18.2°, 19.1° and 23.8°.

As is clear from FIG. 2 and Table 2, the crystals (a-2) of Example 2 also had a peak of maximum intensity at 6.1° and characteristic peaks at 6.1°, 17.7°, 17.9°, 18.2°, 19.1° and 23.8°.

Reference Example 1

To a reaction vessel equipped with a Dean-Stark reflux condenser and a stirrer, 24 ml of methyl isobutyl ketone, 126 ml of methanol and 33.0 g of 3-hydroxy-2-naphthoic acid hydrazide (HNH) were added so that the concentration of HNH was 21.7% by mass. The mixture was heated to about 64° C. and refluxed for 6 hours. The reaction mixture was cooled to 20° C. at a rate of 1.3° C./min, which caused the precipitation of crystals, and then the crystals were aged at about 20° C. for 12 hours. The precipitated crystals were filtered off and dried under reduced pressure to give light yellow crystals (b). The crystals (b) were not the crystals according to the present invention.

The crystals (b) had a melting point of 160.1° C., a specific surface area of 0.9 m$^2$/g, and a mean particle size (D$_{50}$) of 11.7 μm and had a pillar shape.

Rubber Composition and Method for Producing Rubber

The components listed in step (I) in Table 3 were mixed together in the indicated amounts (parts by mass), and the mixture was kneaded in a Banbury mixer for 3 minutes while adjusting the maximum temperature of the mixture to 150° C. by controlling the rotation rate. The mixture was conditioned until the temperature reached 80° C. or less. The components listed in step (II) in Table 3 were then added in the indicated amounts (parts by mass). The mixture was kneaded while adjusting the maximum temperature of the mixture to 110° C. or less to give an unvulcanized rubber composition. The resulting unvulcanized rubber composition was heated in a vulcanizing press at 150° C. for 30 minutes to give a rubber.

Low Heat Build-Up (Low Heat Build-Up Index) Test

The Tan δ value of the rubber of Example formulation 1 was determined using a viscoelastic analyzer (Metravib) at a temperature of 40° C., a dynamic strain of 5% and a frequency of 15 Hz. The Tan δ value of the rubber of Reference formulation 1 was also determined under the same conditions.

The Tan δ value of the rubber of Comparative formulation 1 was also determined under the same conditions, and the resulting value was taken as 100.

The low heat build-up index of each formulation was calculated by the formula below and the results are shown in Table 3. A smaller index indicates a lower heat build-up and a smaller hysteresis loss.

Low heat build-up index={(Tan δ of rubber of Example formulation 1 or Reference formulation 1)/(Tan δ of rubber of Comparative formulation 1)}×100

Mooney Viscosity (Processability Index) Test

The Mooney viscosity of the unvulcanized rubber compositions of Example formulation 1 and Reference formulation 1 was determined using a Mooney viscometer at 100° C. The Mooney viscosity of the unvulcanized rubber composition of Comparative formulation 1 was also determined in the same manner as above, and the resulting value was taken as 100. The processability index was calculated by the formula below and the results are shown in Table 3. A smaller index indicates better processability and higher productivity of an unvulcanized rubber composition.

Processability index={(Mooney viscosity of unvulcanized rubber composition of Example formulation 1 or Reference formulation 1)/(Mooney viscosity of unvulcanized rubber composition of Comparative formulation 1)}×100

TABLE 3

| | | | Example formulation 1 | Reference formulation 1 | Comparative formulation 1 |
|---|---|---|---|---|---|
| Composition | Step (I) | NR (TSR20)*[1] | 100 | 100 | 100 |
| | | CB (N234)*[2] | 45 | 45 | 45 |
| | | Antioxidant*[3] | 1 | 1 | 1 |
| | | Wax*[4] | 2 | 2 | 2 |
| | | Stearic acid*[5] | 2 | 2 | 2 |
| | | Crystals a-1*[6] | 1 | | |
| | | Crystals b*[7] | | 1 | |
| | Step (II) | Vulcanization accelerator (TBBS)*[8] | 1.2 | 1.2 | 1.2 |
| | | Sulfur*[9] | 2 | 2 | 2 |
| | | Zinc oxide*[10] | 3 | 3 | 3 |
| Low heat build-up index | | | 86 | 90 | 100 |
| Processability index | | | 102 | 113 | 100 |

*[1]NR: Natural rubber, TSR20.
*[2]CB (carbon black): N234 (Cabot Corporation)
*[3]Antioxidant: N-phenyl-N'-(1,3-dimethylbutyl)-p-phenylenediamine (Kemai Chemical Co., Ltd.)
*[4]Wax: Antilux 111 (Rhein Chemie Rheinau GmbH)
*[5]Stearic acid (Sichuan Tianyu Grease Chemistry Co., Ltd.)
*[6]Crystals of 3-hydroxy-N'-(1,3-dimethylbutylidene)-2-naphthoic acid hydrazide produced in Example 1.
*[7]Crystals of 3-hydroxy-N'-(1,3-dimethylbutylidene)-2-naphthoic acid hydrazide produced in Reference Example 1.
*[8]Vulcanization accelerator (TBBS): N-(tert-butyl)-2-benzothiazole sulfenamide (SANCELER NS-G, Ouchi Shinko Chemical Industrial Co., Ltd.)
*[9]Sulfur (Shanghai Jinghai Chemical Co., Ltd.)
*[10]Zinc oxide (Dalian Zinc Oxide Co., Ltd.)

As apparent from the results in the table, the rubber of Example formulation 1 containing the crystals (a-1) had improved low heat build-up as compared with that of the rubber of Comparative formulation 1 not containing the crystals of compound A.

The results also demonstrated that the crystals (a-1) of Example formulation 1 can serve as a rubber additive with improved low heat build-up and improved processability as compared with those of another novel crystals (b) of Reference formulation 1.

INDUSTRIAL APPLICABILITY

The crystals of the present invention can be used as a rubber additive capable of imparting low heat build-up properties and other properties to a rubber component without deteriorating processability and are thus very useful in industries.

The invention claimed is:

1. Crystals of 3-hydroxy-N'-(1,3-dimethylbutylidene)-2-naphthoic acid hydrazide having an X-ray powder diffraction pattern comprising a peak of maximum intensity at an angle of diffraction (2θ) of 6.1±0.2°.

2. Crystals of 3-hydroxy-N'-(1,3-dimethylbutylidene)-2-naphthoic acid hydrazide having an X-ray powder diffraction pattern comprising characteristic peaks at least at angles of diffraction (2θ) of 6.1±0.2°, 17.7±0.2°, 17.9±0.2° and 19.1±0.2°.

3. The crystals according to claim 2, wherein the crystals have an X-ray powder diffraction pattern comprising characteristic peaks at least at angles of diffraction (2θ) of 6.1±0.2°, 17.7±0.2°, 17.9±0.2°, 18.2±0.2°, 19.1±0.2° and 23.8±0.2°.

4. The crystals according to claim 1, wherein the crystals have a melting point of 148° C. or more.

5. A rubber additive comprising the crystals according to claim 1.

6. A rubber composition comprising the rubber additive according to claim 5.

7. A tire comprising the rubber composition according to claim 6.

8. A method for producing the crystals according to claim 1, the method comprising
bubbling oxygen gas or an oxygen-containing gas into a solution containing 3-hydroxy-N'-(1,3-dimethylbutylidene)-2-naphthoic acid hydrazide.

9. A method for improving low heat build-up and/or processability of a rubber, the method comprising using the crystals according to claim 1 to improve low heat build-up and/or processability of a rubber.

10. The crystals according to claim 1, wherein the crystals have a mean particle size at 50% ($D_{50}$) of 0.5 μm or more.

11. The crystals according to claim 10, wherein the crystals have a mean particle size at 50% ($D_{50}$) of 0.5 μm to 50 μm.

12. The crystals according to claim 1, wherein the crystals have at least one shape selected from the group consisting of a plate shape, a pillar shape and an acicular shape.

13. The crystals according to claim 12, wherein the crystals have a plate shape.

* * * * *